(12) United States Patent
Krizler et al.

(10) Patent No.: US 10,487,219 B2
(45) Date of Patent: Nov. 26, 2019

(54) METHOD AND COMPOSITIONS FOR CLEANING COOKING RANGE EXHAUST SYSTEMS

(71) Applicant: NOVAPHARM RESEARCH (AUSTRALIA) PTY LTD, Rosebery, New South Wales (AU)

(72) Inventors: Steve Krizler, Rosebery (AU); Andrey Vegera, Kogarah (AU)

(73) Assignee: NOVAPHARM RESEARCH (AUSTRALIA) PTY LTD, Rosebery, New South Wales (AU)

( * ) Notice: Subject to any disclaimer, the term of this patent is extended or adjusted under 35 U.S.C. 154(b) by 0 days.

(21) Appl. No.: 15/736,076

(22) PCT Filed: Jun. 15, 2016

(86) PCT No.: PCT/AU2016/050496
§ 371 (c)(1),
(2) Date: Dec. 13, 2017

(87) PCT Pub. No.: WO2016/201504
PCT Pub. Date: Dec. 22, 2016

(65) Prior Publication Data
US 2018/0163060 A1    Jun. 14, 2018

(30) Foreign Application Priority Data

Jun. 16, 2015 (AU) ................................ 2015902295

(51) Int. Cl.
| | |
|---|---|
| *C09D 5/20* | (2006.01) |
| *C09D 5/14* | (2006.01) |
| *C09D 175/04* | (2006.01) |
| *F24C 15/20* | (2006.01) |
| *C07C 69/78* | (2006.01) |
| *C09D 5/02* | (2006.01) |
| *C09D 131/04* | (2006.01) |
| *C09D 133/08* | (2006.01) |
| *C09D 137/00* | (2006.01) |
| *C09D 163/00* | (2006.01) |

(52) U.S. Cl.
CPC ................ *C09D 5/20* (2013.01); *C07C 69/78* (2013.01); *C09D 5/021* (2013.01); *C09D 5/14* (2013.01); *C09D 131/04* (2013.01); *C09D 133/08* (2013.01); *C09D 137/00* (2013.01); *C09D 163/00* (2013.01); *C09D 175/04* (2013.01); *F24C 15/20* (2013.01)

(58) Field of Classification Search
CPC ...... C09D 5/20; C09D 175/04; C09D 137/00; C09D 163/00; C09D 131/04; C09D 133/08; C09D 5/021; C09D 5/14; C07C 69/78; F24C 15/20
USPC .................................................. 427/154–156
See application file for complete search history.

(56) References Cited

U.S. PATENT DOCUMENTS

| 6,124,044 | A | 9/2000 | Swidler | |
|---|---|---|---|---|
| 2006/0222845 | A1* | 10/2006 | Deng | ..................... A01N 25/34 428/336 |
| 2010/0167075 | A1* | 7/2010 | Mesa | ....................... C09D 5/20 428/524 |
| 2012/0171399 | A1 | 7/2012 | Pai et al. | |

FOREIGN PATENT DOCUMENTS

| CN | 1563225 A | * | 1/2005 |
|---|---|---|---|
| CN | 1259383 C | | 6/2006 |
| CN | 101381545 A | | 3/2009 |
| EP | 1 801 133 A1 | | 6/2007 |
| WO | WO 02/24346 A1 | | 3/2002 |

OTHER PUBLICATIONS

Machine translation of CN 1563225 A using google translate (Year: 2005).*
WO, PCT/AU2016/050496 ISR and Written Opinion, dated Aug. 1, 2016.
WO, PCT/AU2016/050496 Second Written Opinion, dated Jul. 10, 2017.
WO, PCT/AU2016/050496 Response to Second Written Opinion, dated Sep. 11, 2017.
WO, PCT/AU2016/050496 IPRP, dated Oct. 12, 2017.
EP, 16810616.9 Supplementary Search Report, dated Jan. 14, 2019.

* cited by examiner

*Primary Examiner* — Jose Hernandez-Diaz
(74) *Attorney, Agent, or Firm* — One LLP

(57) ABSTRACT

The present invention provides a coating and associated methods for removing fats, oils and cooking effluent from a range exhaust system. The coating may comprise an emulsion or dispersion of a polyvinyl acetate polymer or copolymer, an acrylic polymer or copolymer, a polyepoxy ester, or a styrene acrylic copolymer, or a polymer or copolymer of polyurethane, polyvinylbutyral, or copolymer blends of any of the above. Optionally, the coating also contains an oil soluble biocide which migrates into fats, oils and cooking effluent deposited in use on the surface of said peelable coating. The coating may be applied in the form of an emulsion, dispersion or solution and is preferably formulated for dispensation as an aerosol from a pressure pack container and packaged within a pressure pack container.

19 Claims, No Drawings

METHOD AND COMPOSITIONS FOR CLEANING COOKING RANGE EXHAUST SYSTEMS

CROSS-REFERENCE TO RELATED APPLICATIONS

This application is the National Stage of International Application No.: PCT/AU2016/050496, filed Jun. 15, 2016, which claims priority to Australian Patent Application No. 2015902295, filed Jun. 16, 2015.

BACKGROUND OF THE INVENTION

The present invention relates to a method for cleaning and maintaining cooking range exhaust systems and to compositions for use in the method.

The term "range" as herein used refers to kitchen appliances used for cooking and for preparing hot food and primarily includes surfaces such as those associated with stove tops, griddles and braziers but also may include ovens and the like. A "range hood" is a metal covering above a cooking surface that leads to a vent or exhaust duct. Especially when in commercial use, cooking ranges are usually provided with a cooking range "exhaust system" which generally include one or more range hood exhaust flues, fans ducts and the like, which are used to draw smoke, odour, fats and oils, and other types of cooking effluent away from the cooking surface. In drawing the effluent away from the cooking surface, some of the fat and oil and other substances accumulate on interior surfaces of the exhaust system, that is to say on surfaces of the range hood, on exhaust fans and on exhaust flue surfaces. The interior surfaces of the cooking range hood exhaust flue, and exhaust system parts, when covered in accumulated fats, oils and cooking effluent, can be a significant fire hazard because grease and other highly flammable effluent are retained near a hot cooking surface. It is also a health hazard since the accumulated fats, oils and food particles can drop back onto cooking surfaces to contaminate food and provide an excellent nutrient for growth of microorganisms which can fall onto and contaminate food on the cooking surface, or infect workers in the vicinity and cause unpleasant odours.

Due to the significant fire danger involved in cooking below accumulated fats, oils and other cooking effluent in a cooking range exhaust, the interior surfaces of a range hood, exhaust flue, and other surfaces of the exhaust system should be cleaned regularly. Commercial food preparation installations are required by law in Australia to be cleaned at regular intervals with the regularity of cleaning dependent upon the intensity of use of the cooking equipment. Typically, cooking range exhaust cleaning is performed manually and can be particularly difficult because of the elevated, confined and remote areas involved, such as in the exhaust flue, ducting and fans and in a backsplash in the range hood, as well as on the range hood surfaces. For these reasons, commercial kitchens oftentimes opt to clean cooking areas having difficult to reach cooking range exhaust portions at unsafe periodic intervals, and even at unhygienically long intervals. Cleaning of these difficult to reach areas can be dangerous, costly, messy, and usually requires closure of the kitchen during the cleaning process. A highly problematic aspect of these cleaning processes relates to occupational health and safety because the surfaces to be cleaned are elevated and usually above cooking surfaces which should not be stepped upon even if covered with a drop sheet. The elevated position therefore requires a ladder or ladder system to be employed. The material being cleaned manually from this elevated position involves oils and fats which are inevitably greasy and slippery. Falls and resulting injuries to workers due to slipping from these ladders are well known. Although the invention will be herein described primarily with reference to cooking equipment in commercial use it will be understood that it is applicable to domestic cooking ranges and to apparatus for use for purposes other than food preparation which may have similar requirements.

DISCUSSION OF PRIOR ART

Currently, the usual method for cleaning cooking range exhaust systems involves covering cooking surfaces and surrounding areas with protective tarpaulins, drop sheets, or shields, and then using ladders or scaffolding to access affected surfaces and to scrub the surfaces with high pH alkaline detergent degreasing chemicals and then to wipe the surfaces clean. Often the surfaces require a subsequent clean with a detergent. The workers are required to don protective clothing, and such cleaning is labour intensive, unpleasant work which normally takes many hours for a single installation. For example, a large range used at a chain outlet making and selling hamburgers might typically employ 4 persons for up to 6 hrs (i.e. 24 person hours) per range hood exhaust system. Moreover, as discussed previously, this is inherently dangerous due to the use of alkaline detergents and due to the risks of slipping from heights, as well as from risks of infection. It is also expensive in terms of labour costs, protection costs, consumables costs, and kitchen down time losses.

The state of the art at the date hereof is well confirmed in US patent application 2014/0311476 (filed June 2014) the content of which is included herein by reference. That application addresses substantially the same problem as the present invention but purports to solve it by providing a cleaning system having a fluid delivery system, sprays for directing degreasing compositions onto affected surfaces, and a pumping system to remove the contaminated degreasing agent. This is a costly and complex solution which cannot easily be retrofitted to an installed range exhaust system, which necessitates the use of unpleasant and potentially toxic and dangerous alkaline degreasing chemicals, and which does not provide a simple, easy to use, inexpensive, method for rendering range hood surfaces clean. To the best knowledge of the present inventors, the system proposed in 2014/0311476 is not been being widely adopted, or considered for adoption at the date hereof.

Any discussion of the prior art throughout the specification should in no way be considered as an admission that such prior art is widely known or forms part of common general knowledge in the field.

OBJECT OF THE INVENTION

It is an object of the present invention to overcome or ameliorate at least one of the disadvantages of the prior art, or to provide a useful alternative.

The present invention has as its object to provide a simple, safe, easy to use, method and composition for use in maintaining a range hood in a clean and useable condition. Preferred embodiments of the invention avoid or ameliorate at least some disadvantages of the prior art.

BRIEF DESCRIPTION

According to a first aspect the invention provides a method for removing fats, oils and cooking effluent from a range exhaust system comprising the steps of:

(1) applying an adherent but peelable coating composition to the clean surfaces of the range exhaust system (2) allowing fats, oils or cooking effluent in use of the system to deposit on the surface of said peelable coating for a period, (3) after said period peeling the coating from said system whereby to remove deposited fats, oils or cooking effluent for disposal.

In preferred embodiments, it has been found that the films of the present invention provide a method for much more easily and safely removing fats, oils and cooking effluent from a range exhaust system than current methods of cleaning.

In a related aspect, the invention provides a method for removing fats, oils and cooking effluent from a range exhaust system comprising the steps of:

1) applying an adherent but peelable coating composition in the form of a solution or emulsion to the clean surfaces of the range exhaust system and allowing solvent to evaporate from the solution or emulsion thereby to form a continuous peelable film (2) allowing fats, oils or cooking effluent in use of the system to deposit on the surface of said continuous peelable film, (3) peeling said continuous peelable film from the range exhaust system whereby deposited fats, oils or cooking effluent are removed.

Fats, oils or cooking effluent may be allowed to deposit for any desired period, including advantageously, a period of at least 30 days. However, coatings may be removed after a shorter or longer period if desired. In a preferred method according to the invention steps 1, 2, and 3 may then be repeated without the necessity to clean the range exhaust system surface between the peeling step and the following re-application step.

The present invention provides a peelable coating composition which can be applied to clean interior surfaces of a clean range exhaust system which in use is subsequently exposed to deposit of fats, oils and cooking effluent. The coating composition can be applied by roller, brush, spray or the like and dries to provide a continuous adherent film on the exposed surface or surfaces. The film is able to remain adherent for long periods, that is to say for a period of at least one month and if necessary for several months. While it is in place, fats, oils and other cooking effluent accumulate on the surface of the adherent film instead of on the underlying range hood surfaces which remain clean. At the end of a period the film is peeled off the surface in large sheets, taking with it the accumulated fats, oils and cooking effluent which may then be disposed of. A fresh coating is then applied to the now clean range hood surfaces in preparation for further cooking.

Desirably the period is 30 days or longer.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Peelable film coatings, as such, are known and have been used for example to protect the exterior of automobiles and other products against abrasion, abrasive dust, and exposure to salt and duco affecting chemicals during delivery. See for example EP 1333938 and U.S. Pat. No. 6,124,044 (both to Swidler). However, peel coatings have not been applied to hot surfaces or surfaces which become hot in use for extended periods such as occur on range hoods which may be exposed to flames on the cook surface below. Known peelable coatings have not, to the best of the present inventors' knowledge, been successfully employed or even tried on range hood exhaust systems. To be of use on a range hood exhaust system, a peelable coating would need to be sufficiently adherent not only to a variety of metals including stainless steel, galvanised steel, aluminium, anodised aluminium and copper, but also on materials used in components such as fan blades and the like which are often made of polypropylene, nylon, polyester or other polymers. The composition would need to be able, in use, to withstand exposure to surface temperatures at least as high as 60° C. and more preferably as high as 80° C. for weeks or months while maintaining its inherent strength and flexibility. The coating would need to remain adherent in use for long periods (at least a month) while exposed to such temperatures and while covered with grease, oil and or cooking effluent which tends to cause many films to swell and/or break at elevated temperatures. The coating film needs to be sufficiently easy to peel off and to remain sufficiently strong when peeled off so as to carry off the fats, oils and effluent on it. Desirably the film should be acceptable in land fill.

Known peelable coatings fail to meet one or more of these requirements. Having conceived the idea of applying a peelable coating to a range hood exhaust system for the purpose envisaged, the present inventors extensively investigated known peelable coatings and were unable to find a known formulation satisfactory for the proposed use. Considerable subsequent research was required to develop suitable compositions. It was especially difficult to provide a composition which (1) formed an adherent coating on all the surfaces involved, (2) retained sufficient flexibility to be peeled off after exposure to the conditions encountered in use, (3) retained sufficient mechanical integrity to be peeled off in one piece or in a few large intact pieces, and (4) which possessed sufficient strength and flexibility to carry off and dispose of deposited cooking residues.

According to a second aspect the invention provides a method according to the first aspect wherein a step of applying is repeated after the step of peeling without further cleaning of the surfaces of the range hood exhaust system in the interim.

It was surprising that films according to the invention were removable leaving a surface so clean that a new coating could be applied without interim cleaning, thus producing further cost savings in labour and consumables.

In comparison with the approximately 24 person hours required to clean the large system when the prior art labour intensive method is used, the present invention accomplishes the task in approximately 20 minutes (approximately 5 mins to peel; approximately 15 mins to re-apply), i.e. a greater than approximately 98% reduction in labour cost.

An additional problem affecting range hoods which has not been previously recognised relates to the growth of microorganisms in the oil and grease film on the surface of the range hood, or in the present case on the peelable coating protecting the range hood surface. Such microorganisms are opportunistic and conditions are often ideal for their growth, i.e. warmth, nutrient in the form of vegetable oils, animal fats and cooking effluent as well as moisture coming from the cooking process. Such proliferation of microorganisms can give rise to unpleasant odours as well as presenting a health hazard to diners and staff.

According to a third aspect the invention provides a method according to the first or second aspect wherein the peelable coating incorporates a biocide selected to be oil soluble and which migrates into fats, oils and cooking effluent deposited in use on the surface of said peelable coating.

In preferred embodiments of the method according to the third aspect the peelable coating composition includes one or more oil soluble biocides which leach from the coating into the oil or grease film accumulating on its surface and prevent the replication of microorganisms in the oil or grease on the surface. Biocides have not previously been required in a peelable coating for any purpose other than preservation of the composition and range hoods have not previously enjoyed protection against this health hazard. Preferred biocides are non-hazardous to humans and acceptable for use in a food preparation environment.

According to a fourth aspect the present invention provides a coating composition which is applicable to interior surfaces of a range hood exhaust system and which dries to form an adherent coating film on said surfaces on which fat, oil, and cooking effluent may accumulate, said coating remaining peelable in large pieces and remaining flexible when peeled despite exposure to surface temperatures of up to 60° C., during more than 4 weeks of use Preferred embodiments of the invention remain peelable and flexible despite exposure to surface temperatures of up to 80° C. during more than 1 months of use. More highly preferred embodiments remain peelable and flexible despite exposure to temperatures of up to 80° C. during more than 3 months of use. It will be appreciated that the surfaces of range hood exhaust systems are subjected in use to varying temperatures. Food being cooked is often heated to 100° C. and oil ignition can cause fire flare ups exceeding that temperature near the cooking top. The range hood exhaust system surfaces tend to maintain temperatures averaging up to 60° C. for long periods and sometimes averaging up to 80° C. while cooking is in progress and for some time afterwards, that is to say often for more than 12 hrs a day in commercial operations. They may be subjected to higher temperatures for short times and to lower temperatures during down times. Conventional peelable coatings when applied to the surface of range hood systems in use start to decompose and/or to become increasingly brittle. This is especially the case with polyvinyl acetate based coatings which slowly hydrolyse to polyvinyl alcohol which is well known to become crystalline at elevated temperatures.

According to a fifth aspect the invention provides a composition according to the fourth aspect further comprising at least one oil or fat soluble biocide present in a concentration in excess of that required if any as a preservative.

According to a sixth aspect the invention provides a peelable coating composition according to the fourth or fifth aspect being an emulsion or dispersion or solution comprising one or more of:
 a polyvinyl acetate polymer or copolymer; or
 an acrylic polymer or copolymer; or
 a polyepoxy ester; or
 a styrene acrylic copolymer; or
 a polyurethane polymer or copolymer; or
 a polyvinylbutyral polymer or copolymer; or
 a polyvinylalcohol polymer or copolymer; or blends of any of the above. Highly preferred are peelable coating composition comprising acrylic polymer emulsions or dispersions. Most highly preferred are polyvinyl acetate emulsions, polyvinylbutyral polymer solutions or polyvinylalcohol solutions.

According to a seventh aspect the invention provides a peelable coating composition according to any one of the fourth to sixth aspects incorporating a plasticiser or plasticiser system having low human toxicity and which prevents embrittlement at temperatures of up to at least 60° C. during at least a month, and preferably at temperatures up to 80° C. The present inventors found that prior art peelable coatings, and particularly those based on polyvinyl acetate when used on range hood exhaust systems according to methods herein described became brittle when in place for a month or longer and exposed to temperatures up to, or greater than, about 60° C. and became very difficult to peel off as a single sheet or in usefully large sheets. Attempts to solve this problem by incorporating conventional plasticisers were unsuccessful or resulted in the coating including toxic materials which rendered the composition unsuitable for use in a food preparation hereinafter.

According to an eighth aspect the invention provides a peelable coating composition according to any one of the third to seventh aspects incorporating a plasticiser or plasticiser system having low human toxicity and which prevents embrittlement at temperatures of at least 60° C., said system comprising polyethylene glycol ("PEG") as an embrittlement modifier.

According to a ninth aspect the invention provides a range hood exhaust system having surfaces coated with a peelable coating according to any one of the fourth to seventh aspects.

PREFERRED EMBODIMENTS OF THE INVENTION

The invention will now be more particularly described by way of example only.

Compositions suitable for use in the invention are generally water based paint like compositions which can be painted on to range hood surfaces, and can be applied by brush, roller or spray. They dry within about an hour or two after application at normal ambient temperatures, and form a continuous adherent film on clean metal surfaces as well as on clean plastic surfaces. However, if required the cooking process may commence immediately after coating since the warmth can accelerate the drying of the coating. A reference to a continuous film also includes reference to a film having a number of smaller, continuous sections.

Preferred formulations according to the invention and for use in the method of the invention include, among others, film forming polyvinyl acetate polymer or copolymer emulsion or dispersions. Compositions according to the invention may also be formulated for packaging in pressure pack containers and applied directly by spraying from the pressure pack container.

Peelable coating compositions according to the invention based upon polyvinyl acetate are shown by way of example only in formulations 1 to 8 in Table 1 and formulations 9 to 15 in Table 2.

TABLE 1

| Formulation nr. | 1 | 2 | 3 | 4 | 5 | 6 | 7 | 8 |
|---|---|---|---|---|---|---|---|---|
| Water | 9.2% | 7.6% | 5.9% | 4.2% | 13.2% | 12.8% | 13.2% | 13.2% |
| Clay Bentone LT | 0.5% | 0.1% | 0.6% | 0.0% | 0.5% | 0.9% | 0.5% | 0.5% |
| Fumed Silica | 0.0% | 0.0% | 0.2% | 0.5% | 0.0% | 0.0% | 0.0% | 0.0% |
| Polyvinyl Acetate, (48% solids) - binder | 80.0% | 80.0% | 80.0% | 80.0% | 80.0% | 80.0% | 80.0% | 80.0% |
| Phenoxyethanol | 0.3% | 0.3% | 0.3% | 0.3% | 0.3% | 0.3% | 0.3% | 0.3% |
| Hydrogenated Castor Oil, ethoxylated | 1.0% | 1.0% | 1.0% | 1.0% | 1.0% | 1.0% | 1.0% | 1.0% |
| Eastman 168 Plasticizer* | 5.0% | 3.0% | 1.0% | 1.0% | 1.0% | 1.0% | 1.0% | 1.0% |
| Propyl Parabens | 1.0% | 1.0% | 1.0% | 1.0% | 1.0% | 1.0% | 1.0% | 1.0% |
| Butyl Parabens | 1.0% | 1.0% | 1.0% | 1.0% | 1.0% | 1.0% | 1.0% | 1.0% |
| PEG 600 | 2.0% | 6.0% | 9.0% | 11.0% | 0.0% | 0.0% | 0.0% | 0.0% |
| PEG 1000 | 0.0% | 0.0% | 0.0% | 0.0% | 2.0% | 0.0% | 0.0% | 0.0% |
| PEG 4000 | 0.0% | 0.0% | 0.0% | 0.0% | 0.0% | 2.0% | 0.0% | 0.0% |
| PEG 6000 | 0.0% | 0.0% | 0.0% | 0.0% | 0.0% | 0.0% | 2.0% | 0.0% |
| PEG 8000 | 0.0% | 0.0% | 0.0% | 0.0% | 0.0% | 0.0% | 0.0% | 2.0% |

*Eastman 168 is (bis (2-ethylhexyl terephthalate)

TABLE 2

| Formulation nr | 9 | 10 | 11 | 12 | 13 | 14 | 15 |
|---|---|---|---|---|---|---|---|
| Water | 9.2% | 11.2% | 10.8% | 13.0% | 10.2% | 10.5% | 8.2% |
| Clay Bentone LT | 0.0% | 0.5% | 0.5% | 0.5% | 0.5% | 0.5% | 0.5% |
| Fumed Silica | 0.5% | 0.0% | 0.0% | 0.2% | 0.0% | 0.2% | 0.0% |
| Polyvinyl Acetate. (48% solids) - binder | 0.0% | 80.0% | 80.0% | 80.0% | 80.0% | 80.0% | 80.0% |
| Phenoxyethanol | 0.3% | 0.3% | 0.3% | 0.3% | 0.3% | 0.3% | 0.3% |
| Hydrogenated Castor Oil, ethoxylated | 0.5% | 1.0% | 1.0% | 1.0% | 1.0% | 2.5% | 3.0% |
| Eastman 168 Plasticizer | 5.0% | 0.0% | 0.5% | 1.0% | 5.0% | 5.0% | 5.0% |
| Propyl Parabens | 1.0% | 1.0% | 1.0% | 1.0% | 1.0% | 0.0% | 1.0% |
| Butyl Parabens | 1.0% | 1.0% | 1.0% | 1.0% | 1.0% | 0.0% | 1.0% |
| PEG600 | 2.0% | 0.0% | 0.0% | 1.0% | 1.0% | 1.0% | 1.0% |
| Polyvinyl Acetate/Acrylic (50% solids) - binder | 80.0% | 0.0% | 0.0% | 0.0% | 0.0% | 0.0% | 0.0% |
| TributylPhosphate | 0.0% | 2.0% | 5.0% | 1.0% | 0.0% | 0.0% | 0.0% |

*Eastman 168 is (bis (2-ethylhexyl terephthalate)

The compositions of Table 1 include polyvinyl acetate emulsion (48% solids) in an amount of 80.0% w/w as the binder. Those skilled in the art will understand that this could be varied from around 40% to about 90% and that the solids content of the emulsion may also be varied depending on the intended application method and other factors. The formulations of Table 2 use a polyvinyl acetate/acrylic copolymer as the binder alone or in combination with the polyvinyl acetate emulsion.

Straight acrylic emulsions have been found to be generally unsuitable for use in the present invention, however, polyvinyl acetate/acrylic copolymers can potentially be used in some cases, provided the amount of acrylic portion is relatively low. It will also be understood that other acrylic polymer or copolymer emulsion or dispersion or polyepoxy ester emulsions or dispersion or a styrene acrylic copolymer emulsion or dispersion or a polyurethane polymer or copolymer emulsion or dispersion or blends of any of the above may be able to be suitably formulated. Typically from 75 to 90% of the composition will be the polymer emulsion.

Peelable coating compositions according to the invention based upon polyvinylalcohol are shown by way of example only in formulations 16 to 18 shown in Table 3.

TABLE 3

| Formulation nr | 16 | 17 | 18 |
|---|---|---|---|
| Water | 72.29 | 11.2% | 72.29 |
| Solvent (ethanol) | 0.0% | 71.09 | 0.0% |
| Bentone Clay | 0.3% | 0.5% | 0.3 |
| Fumed Silica | 0.0% | 0.0% | 0.0% |
| Polyvinyl alcohol (highly hydrolysed grade, 86-90%) | 25 | 0.0% | 25.0 |
| Polyvinyl alcohol (ultra low hydrolysis grade, 38-42%) | 0.0% | 25 | 0.0% |
| Phenoxyethanol | 0.0% | 0.3% | 0.0% |
| Castor Oil, ethoxylated | 1.0 | 1.0% | 1.0 |
| Propyl benzoate | 0.2 | 0.2 | 0.2 |
| Butyl benzoate | 0.2 | 0.2 | 0.2 |
| Plasticiser (glycerol or PEG) | 1.0 | 2.0 | 0.0% |
| Plasticiser (glycerol, PEG or urea:triethanolamine mixture) | 0.0% | 0.0% | 1.0 |
| Colourant | 0.01 | 0.01 | 0.01 |

Polyvinyl alcohol may be provided as a film forming agent either in emulsion form or in solution. As shown in the examples, formulations 16 and 18 are provided as aqueous emulsions. Formulation 17 is provided as a solution in ethanol, although any other solvent that allows for suitable application and drying can be used. Both solution and emulsion application provided suitable continuous peelable films.

The fact that polyvinyl alcohol was suitable was somewhat surprising. Normally polyvinylalcohol would not be expected to remain flexible if it was subjected to heating, such as might be encountered in food preparation areas, but rather, it would be expected that polyvinyl alcohol would crystallise. However, it was found that if polyvinyl alcohol was provided in conjunction with a plasticiser, then a very useful peelable film could be provided that has significant cost and other advantages. A number of plasticisers as shown were tried, and the most suitable are nominated in the table above. However, it is believed based on these results that any suitable plasticiser for polyvinyl alcohol can be employed. Chemicals which are commonly used as plasticizers for polyvinyl alcohol include organic compounds such as: glycerol, polyglycols, ethyleneglycol, some of the polyethylene glycols, propylene glycol, polypropylene glycols, ethanol acetamide, ethanol formamide, and ethanolamine salts such as the acetate of triethanolamine and also inorganic salts, for example, like magnesium chloride and magnesium nitrate, which can effectively reduce the internal hydrogen bonding in polyvinyl alcohol and decrease the crystallinity enabling to retain their initial flexibility.

Continuous peelable coating compositions according to the invention based upon polyvinylbutyral are shown by way of example only in formulations 19 to 20 shown in Table 4.

TABLE 4

| Formulation nr | 19 | 20 |
| --- | --- | --- |
| Water | 18 | 11.2% |
| Solvent (ethanol) | 0.0% | 58.00 |
| Bentone Clay (e.g. Bentone EW) | 0.3% | 0.5% |
| Polyvinyl butyral (water dispersion) | 80.0 | 0.0% |
| Polyvinyl alcohol solid resin | 0.0% | 40 |
| Castor Oil, ethoxylated | 0.49 | 0.49% |
| Propyl benzoate | 0.2 | 0.2 |
| Butyl benzoate | 0.2 | 0.2 |
| Plasticiser | 0.6 | 2.0 |
| Colourant | 0.01 | 0.01 |

Polyvinyl butyral may also be provided as a film forming agent either in emulsion form or in solution. As shown in the examples, formulation 19 was provided as an aqueous emulsion. Formulation 20 is provided as a solution in ethanol, although any other solvent that allows for suitable application and drying can be used. Both solution and emulsion application provided suitable continuous peelable films.

In order to ensure that polyvinyl butyral was sufficiently flexible after being subjected to heating in use, it was found desirable to include a plasticiser. Suitable plasticisers include glycerol, PEG or urea:triethanolamine mixtures, although it is believed that any suitable plasticiser can be employed.

Other film forming agents were also tested. Vinyl ether/maleic anhydride copolymers (marketed under the name Gantrez) were also found to be suitable and the results are presented in Table 5.

TABLE 5

| Formulation nr | 21 |
| --- | --- |
| Water | 18 |
| Solvent (ethanol) | 35.09 |
| Bentone Clay (e.g. Bentone EW) | 0.5% |
| Gantrez | 60.0 |
| Castor Oil, ethoxylated | 1.4 |
| Propyl benzoate | 0.35 |
| Butyl benzoate | 0.25 |
| Plasticiser | 2.3 |
| Colourant | 0.01 |

Any of the following Gantrez polymers are believed to be useful: A-425, ES-225, ES-335, ES-425, ES-435 or SP-215

The Gantrez was provided in the form of a solution. Ethanol or isopropanol or mixtures thereof were suitable.

Polyvinyl pyrrolidone/vinyl acetate copolymer solutions were also able to provide continuous films in accordance with the present invention. These are shown in Table 6

TABLE 6

| Formulation nr | 22 |
| --- | --- |
| Water | 18 |
| Solvent (ethanol) | 35.09 |
| Bentone Clay (e.g. Bentone EW) | 0.5% |
| PVP/VA | 60.0 |
| Castor Oil, ethoxylated | 1.4 |
| Propyl benzoate | 0.25 |
| Butyl benzoate | 0.35 |
| Plasticiser | 2.3 |
| Colourant | 0.01 |

Any of the following polyvinyl pyrrolidone/vinyl acetate polymers are believed to be useful: E225, E335, I225, or I335.

A biocide or mixture of biocides may be added to the films of the present invention in order to prevent oil condensing on the film from becoming rancid over time or infecting foodstuffs in the area.

It was determined by the present applicant that the nature of the biocide had a significant effect upon film qualities. Finding a suitable biocide proved to be difficult. Initially biocides were selected for trial on the basis that they would be innocuous in a food preparation area. Many of those initially tested are food grade or similar low toxicity biocides. Biocides were tested by incorporating the biocide in the strippable PV Acetate emulsion coating formulation, coating a film of the coating with cooking oil and leaving it in place for 24 hrs and then testing the oil for presence of Biocide. The leaching of the biocide into the oil is considered a proxy for the ability of the film to prevent microbial degradation of the oily material coated thereon.

Surprisingly, none of the biocides listed below passed the test. Below is a list of biocides which were tried but which proved to be unsuitable.

Biocides which did not migrate from the coating to the oil/grease, and which could be used in the present invention are:

1,3 dichloro 5,5 dimethylhydantoin
Sodium dichloro-isocyanurate
Polyvinyl pyrrolidone iodine complex
Sodium percarbonate
Sodium perborate
Benzoic acid
Sodium benzoate
Sorbic acid
Sodium sorbate
Benzalkonium chloride
Chlorhexidine gluconate
2 bromo 2 nitro 1,3 propanediol
5 chloro 2 methyl 3 isothiazoline Eventually it was found that the most advantageous results could be achieved by selecting an alkyl benzoate (such as methyl benzoate, ethylbenzoate, propyl benzoate and butyl benzoate) biocide. These were effective, passed the above test, and safe to use. Exhaustive testing of biocides was undertaken with polyvinyl acetate emulsions and similar results would be expected for polyvinyl acetate copolymer emulsions, polyvinyl butyral emulsions as well as the films formed from solution.

The alkyl benzoate biocides could be used in any amount, preferably around 0.1 to 5%, more preferably around 0.2 to 3%. Mixtures of benzoates, such as propyl and butyl benzoate have been provided by way of example, however, it is expected that a single alkyl benzoate would be similarly efficacious.

Compositions according to the invention are formulated to be capable of application by rolling, spraying or brushing onto range hood exhaust system surfaces to be treated and to have a suitable viscosity to form a continuous film upon drying.

Amounts of thixotropic agent such as Bentone clay of from 0.1 to 1.0% w/w may be suitable for adjusting the viscosity and flow characteristics of the composition or fumed silica may similarly be employed alone or in combination with the clay or other rheological modifiers. These improve and aid the process of applying the coating composition to the surface, and can improve the thickness homogeneity of the deposited continuous film, however, functional films can be made in every case without the addition of clay or silica. Obtaining a suitable viscosity is important as many rangehood surfaces, for instance, are vertical or angled off the vertical and thixotropic materials will not "sag" or run after spraying. A thicker coating means faster application because a thicker layer of film can be deposited from each spraying pass. If a lower viscosity solution is used, it may take a number of spray passes to achieve the desired film thickness.

Desirably the composition includes a release agent. Alternatives to the Castor oil ethoxylate employed in the exemplified formulations which may be used include castor oil, hydrogenated castor oil ethoxylate, hydrogenated castor oil, lanolin, ethoxylated lanolin, mineral oil, silicone oil, beeswax and the like. Usually amounts of from 0.05% to 5% will be suitable.

The dried film should be able to withstand exposure to temperatures of up to at least 60° C. and be sufficiently strong to be peelable without tearing too easily to facilitate the peeling off of large sections of coating. In the case of dispersions, the preferred liquid carrier is water but alcohols and mixtures of water with alcohol may be used.

In order to provide a suitable range of mechanical strengths, it is preferred if the thickness of the dry film is in the range of 0.2 to 2.0 mm. Although the film still provides protective benefits outside those ranges, films below 0.2 mm do not reliably peel in large strips as is preferred. On the other hand, increasing the film thickness above 2.0 mm provides no additional benefit and forming a film of this thickness or greater would require multiple applications, which would lead to additional time and cost for no advantage over films in the preferred range.

The thickness of 0.2 to 2.0 mm above refers to a film that is largely free of bubbles. The consistency and rheology of the wet coating allows the dry film to incorporate bubbles in which case depending upon the size and number of bubbles in the continuous film, the thickness could be over 2.0 mm and even up to 4.0 mm.

The removed film needs to remain flexible in order to hold the removed fats and grease in place during removal and subsequent disposal. A film which becomes embrittled in situ is difficult to remove from the underlying surface, tears easily, is removable only in small pieces, if at all, and does not allow the clean removal of the accumulated oil and grease. Various plasticisers have been tried in an endeavour to meet this requirement such as Kalama* K-FLEX* 850S from Emerald Performance Materials, LLC: (a mixture of CAS 0000120-55-8 diethylene glycol dibenzoate 65-75 weight % and CAS0027138-31-4 dipropylene glycol dibenzoate 15-20 weight %) and Eastman Texanol™, which is composed of an ester alcohol, namely 2,2,4-trimethyl-1,3-pentanediol mono-(2)-methylpropanoate CAS. No. 25265-77-4. Neither of these plasticisers, both recommended for peelable coating use, withstood the conditions encountered in range hood exhaust systems operation. It has proven very difficult to find satisfactory toxicologically acceptable plasticisers to prevent the applied film from becoming embrittled during use over time at the temperatures involved. The present inventors have found that incorporation of Eastman 168 is (bis (2-ethylhexyl terephthalate) as a plasticiser in an amount of from 0.3% w/w to 5.0% w/w provides a degree of plasticization that is suitable for the use herein described and meets toxicological requirements, but that from 0.1 to 5.0% w/w of polyethylene glycol ("PEG") should be combined with the plasticiser as a crystallinity modifier. The PEG should have a molecular weight in the range 400-8000, but PEG 600 is used in example 1. Other plasticisers with low human toxicity may be substituted for the Eastman 168, for example tributyl phosphate, tributyl citrate and butyl- or propyl-phthalates.

Highly preferred embodiments of the invention include oil soluble biocides and these will be present in a concentration greater than is required for preservation of the emulsion, and the biocide should be selected to be non-toxic to humans and able to be used in a cooking environment. The function of the oil soluble biocide is to leach from the dry film into any oils or oily substances deposited on the surface of the film in situ on the range hood system. These oil soluble biocides then prevent the multiplication of microorganisms in the oil layers that build up on the exterior surface of the strippable coating. To date only propyl and butyl parabens have been found to be satisfactory and they can be used individually or in combination. Surprisingly phenoxyethanol and a number of other biocides expected to function in this way were found to be ineffective. However other oil soluble biocides if toxicologically acceptable to humans may be suitable.

The composition may contain other fillers (such as, talc and the like), colourants, plasticisers, release agents and the like. These fillers will usually comprise from 1.3 to 5% by weight of the composition and colourants up to approximately 1%. The inclusion of colourant or UV light fluorescent substance while not essential is desirable as it assists the applicator to ensure adequate and continuous coverage and removal.

By way of example only of the method, a range hood exhaust system in a busy "fast food" business on which the method has not previously been used was first thoroughly cleaned by traditional means. A peelable coating according to formulation 1 was then applied. The coating was applied by high pressure airless spray gun in a single pass of application. This was a viscous, thixotropic, paint like composition which can be painted on to range hood surfaces, and can be applied by brush or spray. It dries within an hour or two after application at normal ambient temperatures, and forms an adherent film on clean metal surfaces as well as on clean plastic surfaces. However, if required the cooking process may commence immediately after coating since the warmth can accelerate the drying of the coating.

When the range hood needed cleaning, (after about 4 weeks use), a corner of the adhered film was lifted, and the film as a whole was peeled off. The continuous film by then covered with oil, fat, and other cooking residues was peeled from the surface carrying those residues with it. The film could be rolled or folded with the oils fats etc. on the interior and disposed of as normal waste. The range hood cleaning operation took approximately 20 minutes (5 mins to peel and remove the fouled coating and 15 mins to re-apply a fresh peelable coating).

Tests conducted on the cooking residues showed that a bactericidally effective amount of the biocides of formulation 1 had migrated into the oily residues on the film.

A fresh application of a formulation according to the invention may be applied to the range hood surface immediately after removal of the film as above without the need for cleaning of the surface before the new application. Compositions according to the invention may be formulated for packaging and application from an aerosol spray pack by modifications which would be apparent to those skilled in the art from the teaching hereof.

As will be apparent to those skilled in the art from the teaching hereof, the method of the invention can be varied to an extent without departing from the inventive concept herein disclosed. Likewise, the compositions of the invention can be varied, and components substituted, to an extent apparent to those skilled in the art from the teaching hereof without departing from the inventive concept herein disclosed.

The invention claimed is:

1. A method for removing fats, oils and cooking effluent from a range exhaust system comprising the steps of:
   (1) applying an adherent but peelable coating composition to one or more clean surfaces of the range exhaust system
   (2) allowing fats, oils or cooking effluent in use of the system to deposit on the surface of said peelable coating for a period,
   (3) after said period peeling the coating from the range exhaust system whereby to remove deposited fats, oils or cooking effluent for disposal;
   wherein the peelable coating incorporates one or more biocides selected to be oil soluble and which migrate into fats, oils and cooking effluent deposited in use on the surface of said peelable coating; and
   wherein the one or more biocides comprise one or more alkylbenzoates.

2. The method according to claim 1 wherein a step of applying is repeated after the step of peeling without further cleaning of the surfaces of the range hood exhaust system in the interim.

3. The method according to claim 1 wherein the one or more alkylbenzoates are selected from the group consisting of methyl benzoate, ethyl benzoate, propyl benzoate and butyl benzoate.

4. The method according to claim 1 wherein the peelable coating composition dries to form an adherent but peelable coating film on said surfaces on which fat, oil, and cooking effluent may accumulate in use, said coating film remaining peelable and remaining flexible when peeled despite exposure to temperatures of up to 60° C., during more than 4 weeks of use;
   wherein the peelable coating film incorporates one or more biocides selected to be oil soluble and which migrate into fats, oils and cooking effluent deposited in use on the surface of said peelable coating; and
   wherein the one or more biocides are one or more alkylbenzoates.

5. The method according to claim 4 wherein the coating film remains peelable and flexible despite exposure to temperatures of up to 80° C. during more than 3 months of use.

6. The method according to claim 4 wherein the coating film comprises at least one oil soluble biocide present in a concentration in excess of that required if any as a preservative.

7. The method according to claim 4 wherein the oil soluble biocide is non-hazardous to humans.

8. The method according claim 4, wherein the one or more alkylbenzoates are selected from the group consisting of methyl benzoate, ethyl benzoate, propyl benzoate and butyl benzoate.

9. The method according to claim 4 wherein the one or more alkylbenzoates are present in an amount of around 0.1 to 5%.

10. The method according to claim 4 wherein the one or more alkylbenzoates are present in an amount of around 0.2 to 3%.

11. The method according to claim 4 wherein the coating film comprises a polyvinyl acetate polymer or copolymer emulsion or dispersion, an acrylic polymer or copolymer emulsion or dispersion, a polyepoxy ester emulsion or dispersion, a styrene acrylic copolymer emulsion or dispersion, a polyurethane polymer or copolymer, a polyvinylbutyral polymer, or copolymer blends of any of the foregoing.

12. The method according to claim 11 wherein the coating composition is applied in the form of an emulsion, dispersion or solution.

13. The method according to claim 12 wherein the coating composition comprises a poly vinyl acetate emulsion or dispersion.

14. The method according to claim 4, wherein the coating composition further comprises a plasticiser system having low human toxicity and which prevents embrittlement of the coating film during exposure to temperatures of up to at least 60° C. during a period of at least one month.

15. The method according to claim 4, wherein the coating composition further comprises polyethylene glycol as an embrittlement modifier.

16. The method according to claim 4 wherein the coating composition further comprises a colourant.

17. The method according to claim 4 wherein the coating composition is formulated for dispensation as an aerosol from a pressure pack container and packaged within a pressure pack container.

18. The method according to claim 4, wherein the coating film has a thickness of 0.2 mm to 4.0 mm.

19. The method according to claim 4, wherein the coating film has a thickness of 0.2 mm to 2.0 mm.

* * * * *

UNITED STATES PATENT AND TRADEMARK OFFICE
CERTIFICATE OF CORRECTION

PATENT NO. : 10,487,219 B2  
APPLICATION NO. : 15/736076  
DATED : November 26, 2019  
INVENTOR(S) : Steve Kritzler and Andrey Vegera Page 1 of 1

It is certified that error appears in the above-identified patent and that said Letters Patent is hereby corrected as shown below:

On the Title Page

At (72) Inventors, replace "Krizler" with --Kritzler--.

Signed and Sealed this  
Second Day of June, 2020

Andrei Iancu  
*Director of the United States Patent and Trademark Office*